United States Patent [19]

Hokanson et al.

[11] Patent Number: 4,918,100

[45] Date of Patent: Apr. 17, 1990

[54] CL-1957B ANTIBIOTIC COMPOUND AND ITS PRODUCTION

[75] Inventors: Gerard C. Hokanson, Ann Arbor; John P. Schaumberg, Ypsilanti; James C. French, Ann Arbor; Josefino B. Tunac, Troy, all of Mich.

[73] Assignee: Warner-Lambert Company, Morris Plains, N.J.

[21] Appl. No.: 763,577

[22] Filed: Aug. 8, 1985

Related U.S. Application Data

[63] Continuation-in-part of Ser. No. 531,128, Sep. 12, 1983, abandoned.

[51] Int. Cl.[4] .............................................. A61K 31/35
[52] U.S. Cl. ................................. 514/451; 549/294
[58] Field of Search ..................... 549/294; 514/451

[56] References Cited

U.S. PATENT DOCUMENTS 4,550,021 10/1985 Umezawa et al. .

FOREIGN PATENT DOCUMENTS 3419076 7/1985 Fed. Rep. of Germany .

OTHER PUBLICATIONS

Umezawa et al., J. Antibiotics, 37(7), 706–711 (1984).
Komiyama et al., J. Antibiotics, 38(2): 220–223 (1985).
Tunac et al., J. Antibiotics, 38(4): 460–465 (1985).
J. Antibiotics, 38(7): 85–101.
J. Antibiotics, 38(7): 85–105.

*Primary Examiner*—Glennon H. Hollrah
*Assistant Examiner*—Amelia A. Owens
*Attorney, Agent, or Firm*—Ronald A. Daignault

[57] ABSTRACT

A purified isolate of an actinomycete identified as ATCC 39366 is capable of producing the anti-microbial compound CL-1957B which also exhibits antitumor properties.

The antimicrobial compound CL-1957B is produced by cultivating isolate ATCC 39366 under aerobic conditions in a culture medium containing assimilable sources of carbon and nitrogen until a substantial quantity of the CL-1957B compound is produced, and subsequently isolating the compound.

The antibiotic compound CL-1957B, its pharmaceutically acceptable salts, the pharmaceutical compositions comprising this substance together with a pharmaceutically acceptable carrier is also disclosed, as are methods of treating microbial infections and tumors in mammals, employing these pharmaceutical compositions.

2 Claims, 4 Drawing Sheets

CL-1957B ANTIBIOTIC COMPOUND AND ITS PRODUCTION

CROSS-REFERENCE TO RELATED APPLICATIONS

This application is a continuation-in-part of application Ser. No. 531,128 filed Sept. 9, 1983, now abandoned.

BACKGROUND OF THE INVENTION

The present invention relates to an antibiotic compound demonstrating antitumor activity, designated CL-1957B and its pharmaceutically acceptable salts, to a process for the production of said compound, and to a purified isolate of an actinomycete capable of producing this compound.

More particularly, the process of producing the CL-1957B antibiotic compound relates to an aerobic fermentation process using a purified isolate of an actinomycete, identified as isolate ATCC 39366.

SUMMARY OF THE INVENTION

In accordance with one aspect of the present invention, there is provided a purified isolate of an actinomycete having the identifying characteristics of ATCC 39366 which is capable of producing the antibiotic compound CL-1957B.

In another aspect of the invention, there is provided a process for producing CL-1957B by cultivating the isolate of actinomycete identified as ATCC 39366 under aerobic conditions in a medium containing assimilable sources of carbon and nitrogen until a substantial quantity of CL-1957B is produced, and subsequently isolating the compound.

In accordance with another aspect of the invention, there are provided the antibiotic compound CL-1957B and its pharmaceutically acceptable salts, which compounds exhibit both antimicrobial and antitumor properties.

In another aspect of the present invention, there are provided pharmaceutical compositions comprising at least one CL-1957B compound, its pharmaceutically acceptable salts and, optionally, additional antimicrobial and/or antitumor compounds together with a pharmaceutically acceptable carrier.

In a further aspect of the present invention, a method of treating microbial infections in a mammal comprises administering an effective amount of the compound CL-1957B or a pharmaceutically acceptable salt thereof in combination with a pharmaceutically acceptable carrier.

In another aspect of the present invention, a method of treating tumors in mammals comprises administering an effective amount of the compound CL-1957B or a pharmaceutically acceptable salt thereof in combination with a pharmaceutically acceptable carrier.

BRIEF DESCRIPTION OF THE DRAWING

FIGS. 1a, 1b, 1c, and 1d are the ultraviolet, infrared, 360 MHz proton magnetic resonance, and 90.5 MHz $^{13}C$ nuclear magnetic resonance spectra, respectively, of the compound designated CL-1957B.

DETAILED DESCRIPTION

In accordance with the present invention, the CL-1957B antibiotic compound is produced by cultivating a selected isolate of actinomycete, isolate ATCC 39366, under artificial conditions until a substantial quantity of CL-1957B is formed, and subsequently isolating the compound.

The strain of actinomycete suitable for the purpose of this invention was found in a soil sample collected in Pa., U.S.A. This microorganism was isolated from the soil sample using a suitable agar plating medium, one containing salts such as potassium phosphate, magnesium sulfate, and ferrous sulfate, and carbon sources such as glycerol and asparagine. The strain of microorganism was plated onto the agar medium and, once plated, was incubated at a favorable temperature, particularly 45° C., to allow for the development of the soil microorganisms.

The CL-1957B producing organism that was isolated from the soil sample by the agar plating technique is an unidentified isolate of actinomycete and has been deposited with the American Type Culture Collection, Rockville, Md. 20852, where it is being maintained in their permanent culture collection as ATCC 39366. This organism, which produces CL-1957B, is also being maintained as a dormant culture in lyophile tubes, cryogenic vials, and in soil tubes in the Warner-Lambert/Parke-Davis Culture Collection, 2800 Plymouth Road, Ann Arbor, Mich. 48105, where it is designated as culture WP-2053.

The compound CL-1957B, which demonstrates both antimicrobial and antitumor properties, is produced by isolate ATCC 39366 during aerobic fermentation under controlled conditions. The fermentation medium consists of sources of carbon, nitrogen, minerals, and growth factors. Examples of carbon sources are glycerol and various simple sugars, such as glucose, mannose, fructose, xylose, ribose, or other carbohydrate-containing compounds such as dextrin, starch, cornmeal, and whey. The normal quantity of carbon source materials in the fermentation medium varies from about 0.1 to about 10 weight percent.

Nitrogen sources in the fermentation medium are organic, inorganic, or mixed organic-inorganic material. Examples of such materials are cottonseed meal, soybean meal, corn germ flour, corn steep liquor, distillers dried solubles, peanut meal, peptonized milk, and various ammonium salts.

The addition of minerals and growth factors are also helpful in the production of the CL-1957B compound. Examples of fermentation medium mineral additives include potassium chloride, sodium chloride, ferrous sulfate, calcium carbonate, cobalt chloride, and zinc sulfate. Sources of growth factors include various yeast and milk products.

The preferred method for producing the CL-1957B compound is by submerged culture fermentation. According to this embodiment of the invention, the fermentation ingredients are prepared in solution or suspension and the mixture subsequently sterilized by autoclaving or steam heating. The pH of the aqueous medium is adjusted to preferably between about pH 4 and about pH 8 and the mixture cooled following sterilization to a temperature between about 16° C. to about 45° C. The cooled, sterile fermentation medium is inoculated with the organism and thereafter fermentation is carried out with aeration and agitation.

In the submerged culture method, fermentation is carried out in shake-flasks or in stationary tank fermentors. In shake-flasks, aeration is achieved by agitation of the flasks to bring about mixing of the medium with air.

In stationary tank fermentors, agitation is provided by impellers which may take the form of disc turbines, vaned discs, open turbine or marine propellers. Aeration is accomplished by injecting air or oxygen into the agitated mixture.

Adequate production of the CL-1957B compound is normally achieved under these conditions after a period of about two to ten days.

In an alternative embodiment, the CL-1957B compound may also be produced by solid state fermentation of the microorganism.

The following examples are provided to enable one skilled in the art to practice the present invention and are merely illustrative thereof. They are not to be viewed as limiting the scope of the invention as defined by the appended claims.

FERMENTATIVE PRODUCTION OF THE CL-1957B COMPOUND

EXAMPLE 1

The culture of actinomycete (ATCC 39366) of the present invention, following its isolation from the agar plate, was transferred to an agar slant employing CIM 23 medium and incubated at 28° C. for 7 to 14 days.

TABLE I

| Formulation of CIM 23 Medium | |
| --- | --- |
| Amidex corn starch | 10 g |
| N-Z amine, type A | 2 g |
| Beef Extract (Difco) | 1 g |
| Yeast Extract (Difco) | 1 g |
| Cobalt chloride pentahydrate | 20 mg |
| Agar | 20 g |
| Distilled water | 1000 ml |

EXAMPLE 2

A portion of the microbial growth from the agar slant was used to inoculate an 18-mm×150-mm test tube containing 5 ml of SD-05 seed medium. The inoculated seed was shaken at 24° C., 170 rpm, for three to four days.

TABLE II

| Formulation of SD-05 Seed Medium | |
| --- | --- |
| Amberex 1003 (Amber Laboratories) | 0.5% |
| Glucose monohydrate (Cerelose) | 0.1% |
| Dextrin-Amidex B 411 (Corn Products) | 2.4% |
| N-Z Case (Humko Sheffield) | 0.5% |
| Spray-dried meat solubles (Daylin Labs) | 0.3% |
| Calcium carbonate | 0.2% |

EXAMPLE 3

A 1-ml portion of the microbial growth of Example 2 was transferred to a 185-ml shake-tube containing 25 ml of SM-57 screening medium.

TABLE III

| Formulation of SM-57 Screening Medium | |
| --- | --- |
| Sucrose | 1.5% |
| Lactose | 1.0% |
| Peptonized milk | 0.65% |
| Fish meal | 0.35% |
| Torula yeast | 0.25% |

The inoculated shake-tube was incubated at 24° C. for four days with shaking (170 rpm gyratory shaking, 5 cm throw). Production of the CL-1957B compound was observed for the first time in this broth.

To confirm the fermentation activity of the microorganism, a second 50-ml batch of SM-57 screening medium, contained in a 300-ml baffled shake-flask, was inoculated with 2 ml of microbial seed from Example 2. This mixture was incubated at 24° C. for four days with shaking (170 rpm gyratory shaking, 5 cm throw). After four days, the fermentation beer was granular to mycelial in appearance, and the pH was in the range of pH 5.5–6.0.

The antitumor activity of this fermentation broth was assayed at a dilution of 1:100 versus L1210 mouse leukemia cells grown in tissue culture. The assay technique is fully described in *Cancer Chemotherapy Reports*, Part 3, Vol. 3, No. 2 (1972), Deran, Greenberg, MacDonald, Schumacher, and Abbott. A broth which gave L1210 leukemia cell growth rates of 0 to 35%, compared with the growth of these cells under control conditions, was considered active, 0%, most active. The observed activities of the fermentation broth of Example 3 are given in Table IV.

TABLE IV

| Antitumor Activity of Fermentation Broth from Example 3 (As Measured Against L1210 Mouse Leukemia Cells) | |
| --- | --- |
| Sample | % L1210 Cell Growth |
| Broth from shake-tube | 11 |
| Broth from shake-flask | 6 |

The crude fermentation beer from Example 3 was also tested for antimicrobial activity against several microorganisms employing the agar-disc method. The crude beer was found to be active against *Agrobacterium tumefaciens, Alcaligenes viscolactis, Bacillus subtilis, Branhamella catarhalis, Escherichia coli, Micrococcus luteus*, and *Micrococcus lysodeikticus*.

EXAMPLE 4

Two 2-liter shake-flasks, each containing 300 ml of SM-57 screening medium, were inoculated with 12 ml of microbial seed. The flasks were incubated for four days at 24° C. with shaking (170 rpm gyratory shaking, 5 cm throw).

The fermentation beer from the two flasks was pooled and tested for antitumor activity against both L1210 mouse leukemia cells grown in tissue culture and P388 murine lymphocytic leukemia in vivo. Both tests were conducted in accordance with the methods detailed in *Cancer Chemotherapy Reports*, Part 3, Vol. 3, No. 2 (1972) referenced above.

The crude beer was observed to limit L1210 cell growth to 6% in vitro. The results of the P388 in vivo tests appear in Table V. The data are given there in terms of % T/C values where:

$$\%T/C = \frac{\text{median survival time of treated mice}}{\text{median survival time of control mice}} \times 100$$

TABLE V

| Antitumor Activity of Fermentation Broth from Example 4 (As Measured Against P388 Murine Lymphocytic Leukemia In Vivo) | | |
| --- | --- | --- |
| Dilution of Fermentation Beer | Test 1 | Test 2 |
| Undiluted | Toxic | — |
| 1:2 | 66 (Toxic) | 59 (Toxic) |
| 1:4 | 146 | 126 |
| 1:8 | — | 140 |

TABLE V-continued
Antitumor Activity of Fermentation Broth from Example 4 (As Measured Against P388 Murine Lymphocytic Leukemia In Vivo)

| Dilution of Fermentation Beer | Test 1 | Test 2 |
|---|---|---|
| 1:16 | — | 117 |

The production of the CL-1957B compound was monitored throughout the fermentation cycle by assay against L1210 mouse leukemia in vitro, and by measuring antimicrobial activity against several microorganisms. In addition, such fermentation parameters as pH and percent sedimentation were recorded throughout the fermentation cycle. The data are presented in Table VII.

TABLE VII

| Fermentation Time (Hours) | pH | % Sedimentation (Growth) | Inhibition of Growth of Microorganism Inhibition Zone Diameter (mm) (Using 12.7 mm discs) | | | Percent Growth of L1210 Mouse Leukemia Cells at Given Dilution | | | | |
|---|---|---|---|---|---|---|---|---|---|---|
| | | | E. coli | B. subtilis | M. luteus | 1:100 | 1:500 | 1:1000 | 1:2500 | 1:5000 |
| 0 | 6.3 | — | — | — | — | — | — | — | — | — |
| 24 | 6.4 | 4.7 | — | — | — | NA* | — | — | — | — |
| 48 | 5.9 | 7.4 | 21 | 23 | 15 | 5.7 | 1.6 | — | — | — |
| 69 | 5.2 | 8.0 | 19 | 23 | 16 | 6.2 | 0.4 | — | — | — |
| 96 | 5.15 | 8.7 | 19 | 20 | 16 | 5.7 | 0 | — | — | — |
| 120 | 6.0 | 12.0 | 19 | 19 | 17 | — | 0 | 1.5 | 2.8 | 2.9 |
| 144 | 6.1 | 15.3 | 21 | 19 | 17 | — | 0 | 1.3 | 2.9 | 3.2 |

*NA = Not active

EXAMPLE 5

Culture suspension (1 ml) from a cryogenic vial was thawed and aseptically transferred to a 2-liter baffled flask containing 600 ml of SD-05 seed medium. The inoculated flask contents were incubated for 72 hours at 24° C. with shaking (130 rpm gyratory shaking, 5 cm throw).

After 72 hours, the contents of the seed flask were transferred aseptically to a 30-liter jar fermentor containing 16 liters of SD-05 seed medium. The inoculated jar contents were incubated for 24 hours at 24° C. while being stirring at 300 rpm and sparged with air at a rate of 1 vol/vol/min.

EXAMPLE 6

Three 30-liter stirred-jars, each containing 16 liters of PM-10 production medium, were sterilized by autoclaving for 40 minutes at 121° C. The fermentors and contents were cooled and each was inoculated with about 800 ml of the microbial growth from Example 5. The inoculated production jars were incubated for six days at 24° C. while being stirred at 300 rpm and sparged with air at a rate of 1 vol/vol/min. Dow Corning "C" antifoam agent was used to control foaming.

TABLE VI

| Formulation of PM-10 Production Medium | |
|---|---|
| Maltose | 1.5% |
| Glucose monohydrate | 1.0% |
| Cotton seed meal (Pharmamedia) | 0.75% |
| Corn meal | 0.4% |
| Torula yeast | 0.25% |

Note: pH adjusted to 6.5 with NaOH

EXAMPLE 7

A 1-ml portion of a cryogenically preserved culture of isolate ATCC 39366 was used to inoculate 600 ml of SD-05 seed medium contained in a 2-liter baffled shake-flask. The inoculated shake-flask contents were incubated for 71 hours at 24° C. with shaking (130 rpm gyratory shaking, 5 cm throw).

The microbial growth from the 2-liter flask was used to inoculate 16 liters of SD-05 seed medium contained in a 30-liter stirred jar fermentor. The inoculated fermentor contents were incubated at 24° C. for 24 hours while being stirred at 300 rpm and sparged with air at a rate of 1 vol/vol/min.

A 200-gallon (757-liter) fermentor containing 160 gallons (606 liters) of PM-10 production medium was sterilized by heating with steam for 40 minutes at 121° C. The fermentor and its contents were cooled to 24° C. and inoculated with about 15 liters of the microbial growth from the 30-liter stirred jar fermentor. The inoculated production medium was incubated at 24° C. for five days with stirring at 155 rpm while being sparged with air at a rate of 0.75 vol/vol/min. Dow Corning "C" antifoam agent was added as needed to control foaming of the fermentation medium.

The production of the CL-1957B compound was monitored throughout the fermentation cycle using the L1210 mouse leukemia cell assay, by measuring the antimicrobial activity of the fermentation beer against *Micrococcus luteus* and *Bacillus subtilis*, and by such fermentation parameters as pH and percent sedimentation. The data appear in Table VIII.

TABLE VIII

| Fermentation Time (Hours) | pH | % Sedimentation (Growth) | Inhibition of Growth of Microorganism Inhibition Zone Diameter (mm) (Using 12.7 mm discs) | | Percent Growth of L1210 Mouse Leukemia Cells at Given Dilution | | | |
|---|---|---|---|---|---|---|---|---|
| | | | Micrococcus luteus | Bacillus Subtilis | 1:100 | 1:500 | 1:2500 | 1:5000 |
| 0 | 6.35 | — | — | — | — | — | — | — |
| 26 | 6.65 | 4.7 | 0 | 0 | NA* | — | — | — |
| 52 | 6.10 | 7.4 | 14.0 | 20.5 | 5.0 | 4.5 | — | — |

TABLE VIII-continued

| | | | Observed Bioactivity | | | | | |
|---|---|---|---|---|---|---|---|---|
| | | | Inhibition of Growth of Microorganism Inhibition Zone Diameter (mm) (Using 12.7 mm discs) | | Percent Growth of L1210 Mouse Leukemia Cells at Given Dilution | | | |
| Fermentation Time (Hours) | pH | % Sedimentation (Growth) | Micrococcus luteus | Bacillus Subtilis | 1:100 | 1:500 | 1:2500 | 1:5000 |
| 72 | 6.0 | 8.7 | 16.5 | 21.5 | 6.8 | 3.8 | — | — |
| 96 | 5.9 | 11.3 | 16.5 | 23.5 | — | 5.5 | 5.0 | 16.4 |
| 116 | 6.0 | 14.7 | 18.0 | 20.0 | — | 0 | 3.8 | 3.1 |

*NA = Not active

The crude beer was harvested, and the CL-1957B compound isolated as described below.

CHEMICAL ISOLATION OF THE CL-1957B COMPOUND

EXAMPLE 8

Fermentation beer as prepared above in Example 7 was adjusted to pH 3.5 with sulfuric acid and mixed for one hour with ethyl acetate (227 liters). Celite 545 (11.4 kg) was added and the mixture filtered through a 46-cm plate-and-frame filter press. The filtrate was allowed to stand to let the lower aqueous phase separate from the ethyl acetate extract. The filter cake was washed with ethyl acetate (132 liters) and the wash, after dilution with 76 liters of fresh ethyl acetate, was used to extract the separated aqueous layer from above. After allowing the mixture to settle, the aqueous and organic layers from the second extract were separated and the aqueous layer extracted a third time with fresh ethyl acetate (189 liters). The three organic layers were combined and washed with deionized water (95 liters). The mixture was allowed to settle and the water wash separated. The upper ethyl acetate layer (529 liters) was concentrated in vacuo to 31 liters and then concentrated further with the displacement of ethyl acetate by methanol to yield 4.5 liters of a methanolic concentrate. This concentrate, diluted with one-tenth volume of water, was extracted two times with four liter portions of petroleum ether (bp 30°–60° C.) and then concentrated to approximately 500 ml. Continued concentration with displacement of methanol by water yielded approximately 400 ml of an aqueous suspension which was extracted three times with 400 ml portions of ethyl acetate. The ethyl acetate extracts were combined, dried over anhydrous sodium sulfate, filtered, concentrated to a small volume, and then mixed with 250 grams of a mixture of silicic acid and Celite 545 (1:1). The resulting slurry was evaporated in vacuo to a dry solid which was slurried with dichloromethane (300 ml), and added to the top of a column containing 4 kg of a mixture of silicic acid and Celite 545 (1:1) packed in dichloromethane. The column was washed with dichloromethane (16 liters) and then eluted with dichloromethane-methanol (99:1, 14 liters), dichloromethane-methanol (98:2, 20 liters) and dichloromethane-methanol (96:4, 20.5 liters). Concentration of the dichloromethane-methanol (96:4) eluates afforded a viscous oil containing CL-1957B.

PURIFICATION OF CL-1957B

EXAMPLE 9

The crude CL-1957B fraction from silicic acid-Celite chromatography was triturated two times with 500-ml portions of n-heptane. The heptane insoluble material (18.9 g) was chromatographed over 750 g of silica gel 60 (40–60 $\mu$m particle size, E. Merck Reagents) deactivated with 1% water, contained in a 6 cm [i.d.]$\times$60 cm column. The column was eluted with dichloromethane-methanol (95:5), collected in nine 500-ml fractions. Fractions six and seven, which contained most of the CL-1957B (as determined by HPLC and TLC assay), were combined and concentrated to dryness to yield 4.6 g of partially purified residue. Further purification was effected by chromatography over 1.9 kg of $C_{18}$-silica gel (Sepralyte C-18, 40 $\mu$m particle size, Analytichem International) contained in a stainless steel column (7 cm [i.d.]$\times$85 cm). The column was eluted with methanol-water (7:3), collected in sixteen one-liter fractions. Fractions eleven through fifteen, which contained most of the CL-1957B (by HPLC assay), were combined and concentrated to yield 1.7 g of purified CL-1957B as a light tan solid foam.

Figure 1A:
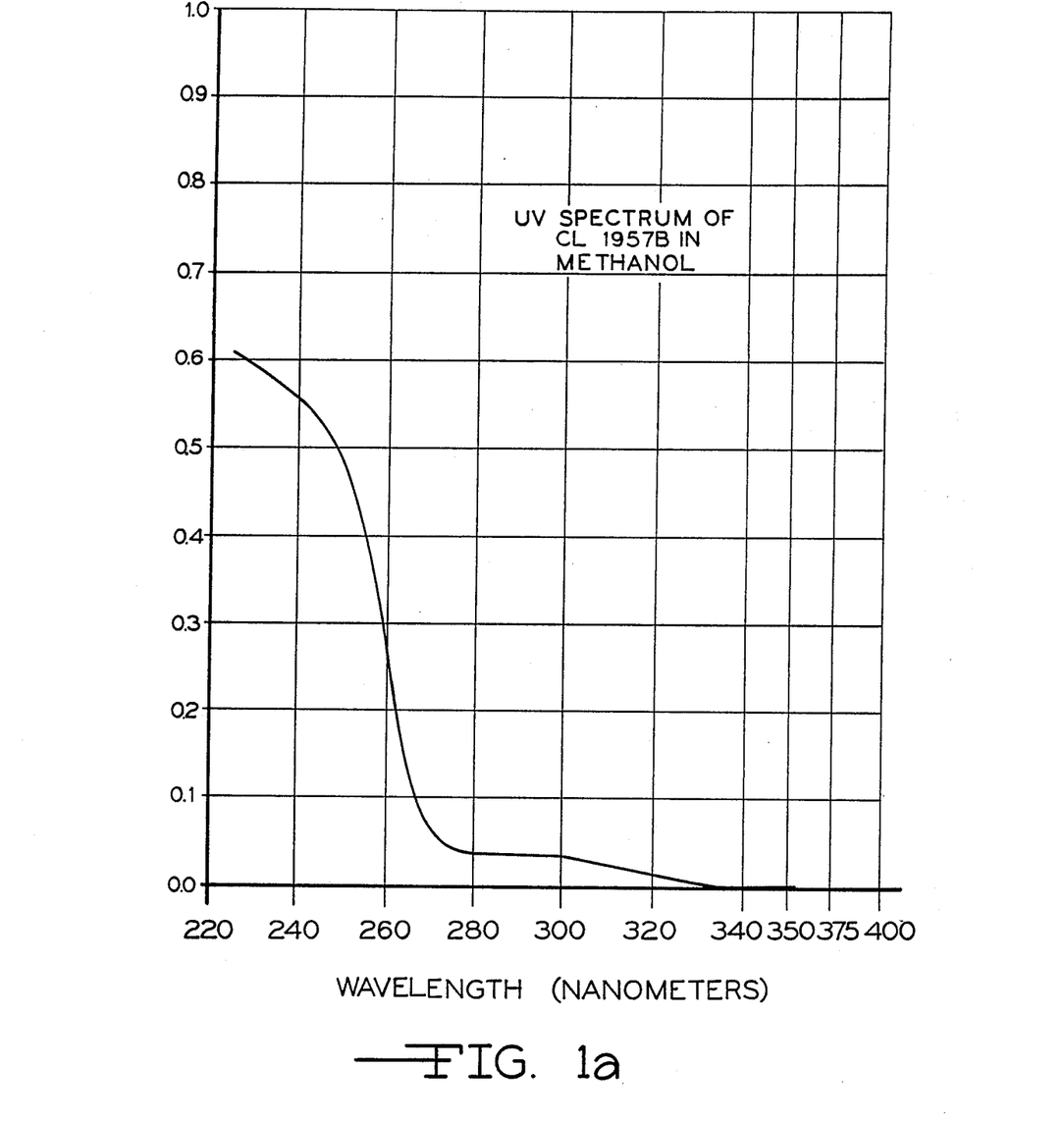
Figure 1B:
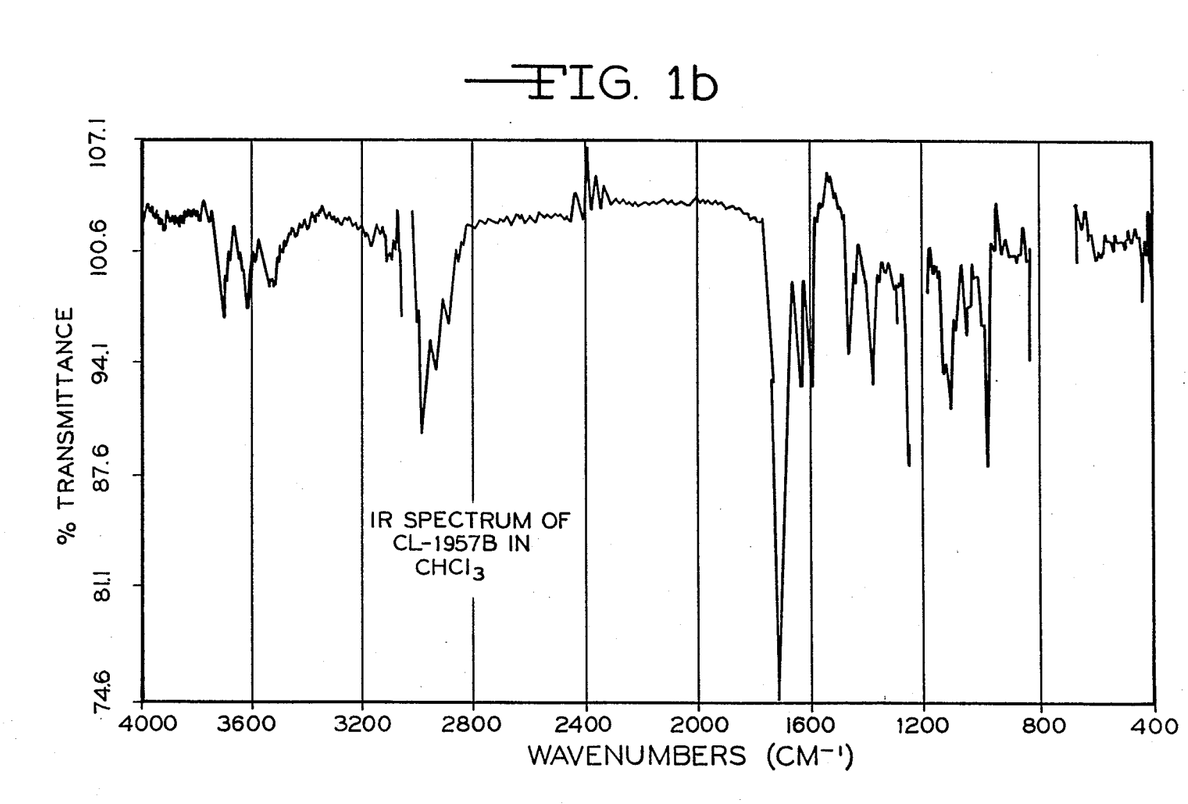
Figure 1C:
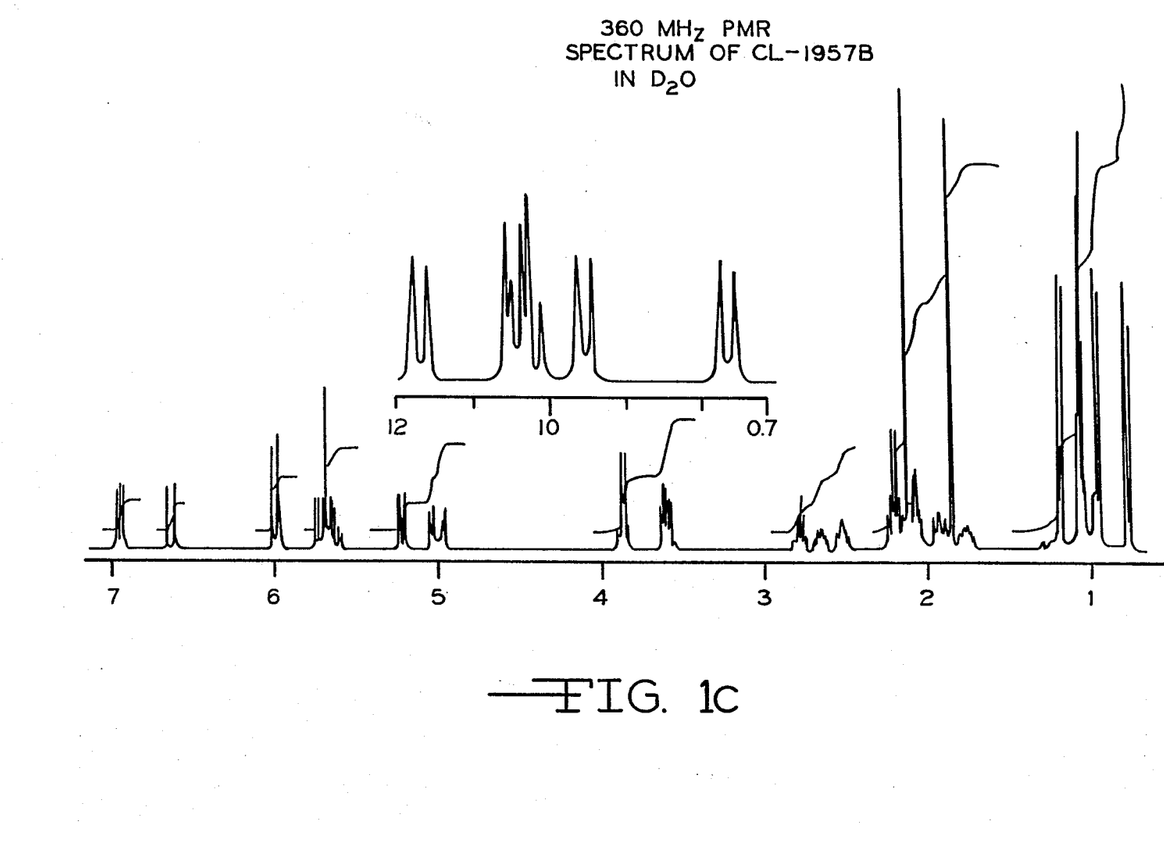
Figure 1D:
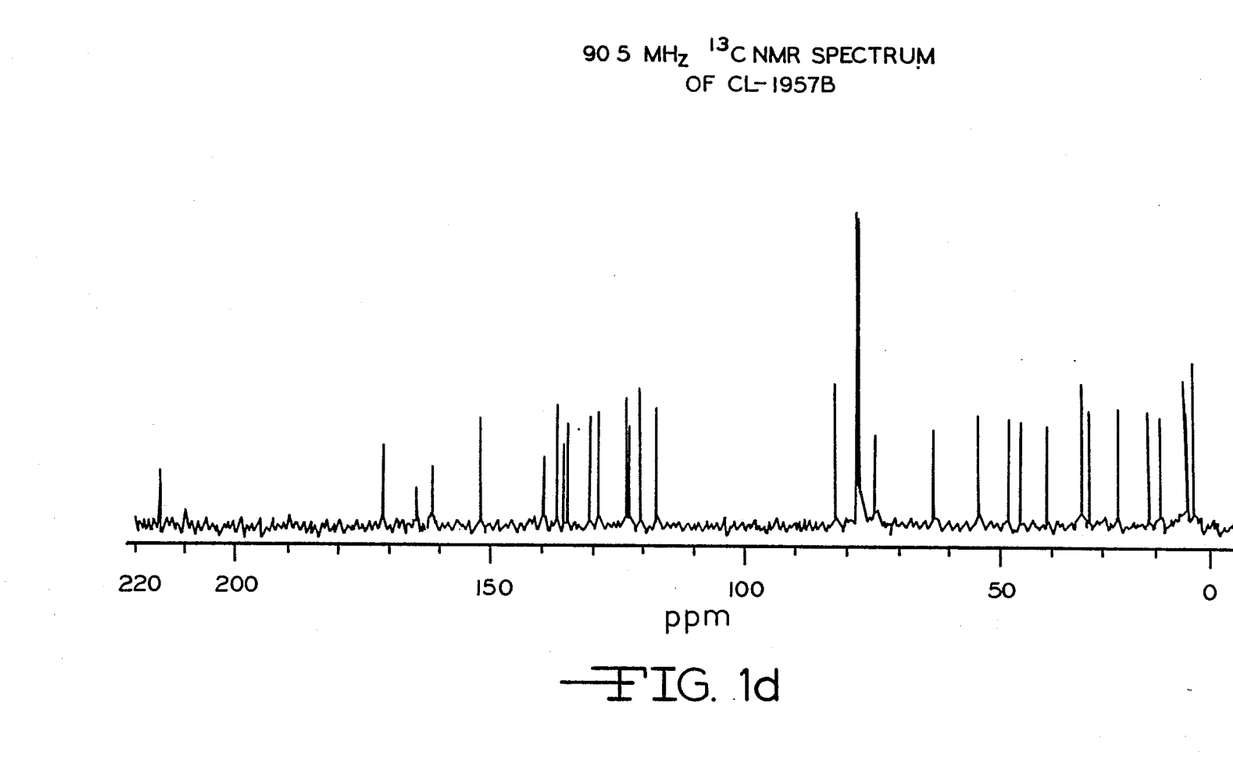

The chemical and physical properties of CL-1957B appear in Table IX and the ultraviolet, infrared, 360 MHz proton magnetic resonance, and 90.5 MHz $^{13}$C nuclear magnetic resonance spectra of the compound appear as FIGS. 1a, 1b, 1c, and 1d, respectively.

TABLE IX

| Chemical and Physical Properties of CL-1957B | |
|---|---|
| Property | CL-1957B |
| Molecular weight | 556 atomic mass units |
| Elemental analysis* | Calculated for $C_{33}H_{48}O_7 \cdot 0.32$ $CHCl_3$: 67.28% C, 8.13% H, 5.73% Cl. Found: 66.92% C, 8.21% H, 5.62% Cl. |
| Melting point | 49°–52° C. (with prior softening) |
| Optical rotation | $[\alpha]_D^{23} = -157°$ (0.7% in chloroform) |
| Ultraviolet absorption spectra | Free acid form (in methanol): Absorption maximum at 289 nm (a = 0.33); end absorption below 260 nm. Carboxylate form (in methanol): Maxima at 240 nm (inflection), 280 nm (a = 0.75), and 385 nm (a = 0.24). |
| Infrared absorption spectrum (in chloroform) | Principal absorption peaks at 2970, 2940, 1715, 1700 (shoulder), 1640, 1455, 1375, 1250, 1100, and 965 reciprocal centimeters. |
| 360 MHz proton magnetic | Principal signals at 0.76 (doublet, 3 protons), |

TABLE IX-continued
Chemical and Physical Properties of CL-1957B

| Property | CL-1957B |
| --- | --- |
| resonance spectrum (deuterochloroform solution) | 0.95 (doublet, 3 protons), 1.03 (triplet, 3 protons), 1.05 (doublet, 3 protons), 1.17 (doublet, 3 protons), 1.74 (multiplet, 1 proton), 1.84 (singlet, 3 protons), 1.91 (doublet of doublets, 1 proton), 2.06 (multiplet, 2 protons), 2.11 (singlet, 3 protons), 2.15 (multiplet, 1 proton), 2.18 (quartet, 2 protons), 2.52 (multiplet, 1 proton), 2.65 (multiplet, 1 proton), 2.78 (multiplet, 1 proton), 3.60 (multiplet, 2 protons), 3.85 (multiplet, 2 protons), 4.96 (doublet of doublets, 1 proton), 5.02 (doublet, 1 proton), 5.20 (doublet, 1 proton), 5.61 (doublet of doublets, 1 proton), 5.66 (singlet, 1 proton), 5.69 (doublet of doublets, 1 proton), 5.98 (doublet, 1 proton), 5.99 (doublet, 1 proton), 6.61 (doublet, 1 proton, and 6.93 (doublet of doublets, 1 proton) parts per million downfield from tetramethylsilane. |
| 90.5 MHz $^{13}$C nuclear magnetic resonance spectrum (deuterochloroform solution) | Principal signals at 214.97, 170.60, 164.40 160.95, 151.97, 139.36, 136.80, 135.62 134.90, 130.26, 128.90, 122.69, 122.08, 120.03, 116.81, 81.55, 73.99, 62.61, 53.84 47.96, 45.66, 40.82, 33.64, 33.56, 32.22 26.61, 20.92, 18.67, 13.63, 13.58, 13.33, 12.39, and 12.32 parts per million downfield from tetramethylsilane. |
| Retention time (high pressure chromatography, μBondpak ™ C18-silica gel column, 3.9 mm i.d. × 30 cm, Waters Associates, Milford, MA, solvent: 45:55 0.05 M ammonium acetate buffer (pH 6.5)-acetonitrile, flow rate 1.5 ml/min) | 4.00 minutes |
| $R_f$ (thin-layer chromaatography on silica gel 60 F254, E. Merck, solvent 90:10 chloroform-methanol) | 0.33 |

*Elemental analysis calculated on the basis of included chloroform solvent of crystallization While not holding to particular structures to the exclusion of others, the chemical structure of CL-1957B is believed to correspond to that indicated by structure I below, which is consistent with the spectral data presented in Table IX.

I (CL-1957B)

The exact cis-trans configuration of the groups attached to the lactone ring and the exact E-Z configurations about the carbon-carbon double bonds are not known with certainty at the time of filing of the present application. The present invention is therefore contemplated as encompassing all possible cis-trans and E-Z isomers of structure I given above. The name of the compound designated above (while not specifying cis-trans or E-Z configuration) is 19-(3,6-dihydro-3-methyl-6-oxo-2H-pyran-2-yl)-17-ethyl-6-hydroxy-9-(hydroxymethyl)-3,5,7,11,15-pentamethyl-8-oxo-2,10,12,16,18-nonadecapentaenoic acid.

The compounds of the present invention possess both an acidic carboxylic acid functional group and a lactone ring. Pharmaceutically acceptable salts of the carboxylic acid function may be prepared without opening the labile lactone ring by either of two methods. In one method, the pH of an aqueous or alcoholic-aqueous solution of the compound is carefully upwardly adjusted by addition of a solution of the appropriate base to a value above the $pK_a$ of the carboxylic acid functionality. This effectively converts the carboxylic acid group to its corresponding carboxylate salt form without raising the pH to a level which causes the ring-opening of the lactone. The solution is then evaporated under vacuum to recover the salt of the carboxylic acid function, with the lactone group intact.

In the alternative method, an aqueous solution of a salt of the carboxylic acid function, such as the sodium salt prepared as described above, is passed through an ion exchange resin in the cation form which has been loaded with the desired cation. This method is particularly adapted for the formation of salts with ammonium or quaternary organic ammonium salts. A suitable resin for this purpose is Dowex-50 (Dow Chemical Company, Midland, Mich., U.S.A.). Procedures for conditioning the resin prior to use, and for converting it to a particular cationic form are available from the manufacturer and are well known to practitioners of the organic chemical arts.

Examples of suitable inorganic bases are ammonium hydroxide, sodium hydroxide, potassium hydroxide, sodium carbonate, calcium hydroxide, sodium bicarbonate and the like. Pharmaceutically acceptable salts of the carboxylic acid funtionality of compounds of the present invention are also formed with amine cations derived from organic nitrogenous bases strong enough to form cations.

The term, pharmaceutically acceptable metal cation contemplates the positively charged ions derived from such metals as sodium, potassium, calcium, magnesium, aluminum, zinc, iron, and the like. The salts are prepared by contacting the free acid form of the compound with an equivalent amount of the desired base in the conventional manner. The free acid form may be regenerated by treating the salt form with an acid. For example, dilute aqueous acid solutions may be utilized to regenerate the free acid form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purposes of the invention.

The term pharmaceutically acceptable amine cation contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

wherein $R_a$, $R_b$, and $R_c$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about 2 to about 4 carbon atoms, or monoarylhydroxyalkyl of from about 8 to about 15 carbon atoms, or, when taken together with the nitrogen atom to which they are attached, any two of $R_a$, $R_b$, and $R_c$ may form part of a 5- to 6-membered heterocyclic ring containing carbon, hydrogen, oxygen, or nitrogen, said heterocyclic rings and said aryl groups being unsubstituted or mono- or dialkyl substituted said alkyl groups containing from about one to about six carbon atoms. Illustrative therefore of $R_a$, $R_b$, and $R_c$ groups comprising pharmaceutically acceptable cations derived from ammonia or a basic amine are ammonium, mono-, di-, and trimethylammonium, mono, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, pyridinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethyldiethanolammonium, n-butylmonoethanolammonium, tris(hydroxymethyl)-methylammonium, phenylmonoethanolammonium, and the like.

BIOLOGICAL ACTIVITY OF CL-1957B

EXAMPLE 10

The antimicrobial activity of CL-1957B was evaluated by saturating 12.7 mm paper discs with solutions of CL-1957B prepared at concentrations of 10, 100, and 500 μg/ml and placing each saturated paper disc on a bioassay tray containing an agar medium seeded with a particular organism. The disc and inoculated medium were incubated for 16 hours at 37° C. and the diameter of the resulting growth inhibition zone, if any, was measured. The data from these tests appear in Table X.

TABLE X

| | | | Diameter of Inhibition Zone (mm) CL-1957B | | |
|---|---|---|---|---|---|
| Microorganism | Culture Number* | Medium | 500 μg/ml | 100 μg/ml | 10 μg/ml |
| Alcaligenes viscolactis | ATCC 21698 | Mycin | 0 | 0 | 0 |
| Bacillus subtilis | ATCC 6633 | #169 | 21 | 0 | 0 |
| Bacillus subtilis | PD 04969 | #169 | 15 | 0 | 0 |
| Bacillus subtilis | ATCC 6633 | Mycin | 0 | 0 | 0 |
| Escherichia coli | ATCC 10563 | GAA | 0 | 0 | 0 |
| Kloeckera brevis | PD M1378 | #69 | 0 | 0 | 0 |
| Branhamella catarrhalis | PD 03596 | CAP | 27 | 14 | 0 |
| Penicillium avellaneum | PD M2988 | H & B | 0 | 0 | 0 |
| Proteus vulgaris | PD 05062 | PAS | 0 | 0 | 0 |
| Micrococcus luteus | PD 05064 | PAS | 14 | 0 | 0 |
| Staphylococcus aureus | PD 02482 | PAS | 20 | 0 | 0 |
| Staphylococcus aureus | PD 5045 | AM-10 | 28 | 18 | 0 |
| Staphylococcus aureus | PD 5045 | AM-9 | 26 | 26 | 0 |
| Xanthomonas phaseoli | PD 06002 | CMA | 0 | 0 | 0 |

*ATCC = American Type Culture Collection, Rockville, Maryland 20852
PD = Warner-Lambert/Parke-Davis Culture Collection, 2800 Plymouth Road, Ann Arbor, Michigan 48105

EXAMPLE 11

The in vivo activity of CL-1957B against P388 against P388 leukemia in mice, was assayed using the protocol established in Cancer Chemotherapy Reports, Vol. 3, Part 3, 1-87 (1972). The mice were infected intraperitoneally on Day 0 and then given the dose of CL-1957B indicated in Table XI on Days 1-5. The results of these tests are presented in Table XI in terms of % T/C values as defined above.

TABLE XI

In Vivo Activity of CL-1957B
Against P388 Leukemia in Mice

| CL-1957B Dose (μg/kg/ injection) | % T/C Test-1 | % T/C Test-2 |
| --- | --- | --- |
| 200 | Toxic | Toxic |
| 100 | 154 | Toxic |
| 50 | 143 | 161 |
| 25 | 139 | 148 |
| 12.5 | 111 | 136 |

EXAMPLE 12

The cytotoxicity of CL-1957B against L1210 mouse leukemia cells and against human colon adenocarcinoma cells were measured in vitro. The $ID_{50}$ values appear in Table XII.

TABLE XII

| Compound | $ID_{50}$ L1210 Mouse Leukemia Cells | $ID_{50}$ Human Colon Adenocarcinoma Cells |
| --- | --- | --- |
| CL-1957B | 0.185 ng/ml | 0.13 ng/ml |

EXAMPLE 13

In this Example, the in vivo activity of CL-1957B was tested against Ridgway Osteogenic Sarcoma in mice as follows. Male AKR mice were pooled, inoculated subcutaneously by trocar with 30 to 60 mg fragments of Ridgway Osteogenic Sarcoma, repooled, and randomly distributed to treat groups on Day 0.

Appropriate mice received intraperitoneal injections of the test compound dissolved in 0.9% sodium chloride solution on Days 2, 6, and 10, and then weekly thereafter. Tumors were measured on Days 24 and 35. The results are presented in Table XIII as % T/C (as defined below.) % T/C values of less than 40 on Day 35 are considered active.

$$\%T/C = \frac{\text{Tumor size of test animals}}{\text{Tumor size of control animals}} \times 100$$

EXAMPLE 14

The in vivo activity of CL-1957B against B16 melanoma in mice was tested using the protocol established in Cancer Chemotherapy Reports, Vol. 3, Part 3, 1–87 (1972). Mice were inoculated by trochar with B16 melanoma on Day 0 and then given intraperitoneal injections of CL-1957B on Days 1, 5, and 9. The activity of the compound against B16 melanoma is present in Table XIV in terms of % T/C values which represents the ratio of median life span in days of treated mice to untreated mice, expressed as a percentage.

TABLE XIV

Activity of CL-1957B Against B16 Melanoma in Mice

| Dose (mg/kg of body weight/injection) | % T/C |
| --- | --- |
| 0.75 | 18 |
| 0.375 | 141 |
| 0.188 | 141 |
| 0.094 | 151 |

The antimicrobial compound CL-1957B, either in its free acid form, or in the form of one or more of its pharmaceutically acceptable salts, is useful for its antimicrobial and antitumor activity as pharmaceutical compositions in combination with a compatible pharmaceutically acceptable carrier. These compositions may also contain other antimicrobial and/or antitumor agents. The compositions may be made up in any pharmaceutically appropriate form for the desired route of administration. Examples of such forms include solid forms for oral administration as tablets, capsules, pills, powders and granules, liquid forms for topical or oral administration as solutions, suspensions, syrups, and elixirs, and forms suitable for parenteral administration such as sterile solutions, suspensions, or emulsions.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 5 to 100 mg according to the particular application and the potency of the active ingredient. The compositions can, if desired, also contain other compatible therapeutic agents.

In therapeutic use, the mammalian dosage range for a 70 kg subject is from 1 to 1500 mg/kg of body weight per day or preferably 2 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

EXAMPLE 15

Preparation of the Sodium Salt of CL-1957B

Cooled aqueous sodium hydroxide solution is added dropwise to a cooled solution of an equimolar amount of CL-1957B compound in methanol. During the addition, a white precipitate forms which redissolves at the end of the addition of base. The resulting solution is concentrated under vacuum and diluted with water. The resulting aqueous solution is divided among several vials, if desired, and lyophilized to yield the sodium salt of CL-1957B as a white solid.

EXAMPLE 16

Preparation of the Calcium Salt of CL-1957B

Cooled aqueous calcium hydroxide solution is added to a methanol solution containing twice the molar amount of CL-1957B compound. Following the addition of the base, the methanol is removed under vacuum, and 1,1-dimethylethanol is added to completely dissolved the precipitate which forms. The resulting solution is lyophilaized to yield the calcium salt.

EXAMPLE 17

Preparation of the Potassium Salt of CL-1957B

Cooled aqueous potassium hydroxide solution is added dropwise to a cooled solution of an equimolar amount of CL-1957B compound in methanol. During the addition, a white precipitate forms which redissolves at the end of the addition of base. The resulting solution is concentrated under vacuum and diluted with water. The resulting aqueous solution is divided among several vials, if desired, and lyophilized to yield the potassium salt of CL-1957B as a white solid.

EXAMPLE 18

Preparation of the Triethylammonium Salt of CL-1957B

A cooled solution of triethylamine in water is added dropwise with stirring to a solution of an equimolar amount of CL-1957B compound in methanol. The resulting solution is concentrated to a final volume of 2 ml on a rotary evaporator and the residue is diluted with water. The resulting solution is lyophilized to yield the triethylammonium salt of CL-1957B as a solid.

We claim:

1. An antimocrobial compound designated CL-1957B, or a pharmaceutically acceptable salt thereof; compound CL-1957B having the name 19-(3,6-dihydro-3-methyl-6-oxo-2H-pyran-2-yl)-17-ethyl-6-hydroxy-9-(hydroxymethyl)-3,5,7,11,15-pentamethyl-8-oxo-2,10,12,16,18-nonadecapentaenoic acid and characterized by:

(a) a molecular weight of 556 atomic mass units;
(b) a melting point of 49°–52° C. (with prior softening);
(c) an optical rotation, $^{23}D$ of $-156°$ (0.82% in chloroform);
(d) an ultraviolet absorption spectrum in methanol (free acid form) showing an absorption maximum at 289 nm (a=0.33) and end absorption below 260 nm;
(e) an ultraviolet absorption spectrum in methanol (carboxylate anion form) showing maxima at 240 nm (a=0.75), and 385 nm (a=0.24);
(f) an infrared spectrum in chloroform solution showing principal absorption peaks at 2970, 2940, 1715, 1700 (shoulder), 1640, 1455, 1375, 1250, 1100, and 965 reciprocal centimeters;
(g) a 360 MHz proton magnetic resonance spectrum in deuterochloroform solution showing signals at 0.76 (doublet, 3 protons), 0.95 (doublet, 3 protons), 1.03 (triplet, 3 protons), 1.05 (doublet, 3 protons), 1.17 (doublet, 3 protons), 1.74 (multiplet, 1 proton), 1.84 (singlet, 3 protons), 1.91 (doublet of doublets, 1 proton), 2.06 (multiplet, 2 protons), 2.11 (singlet, 3 protons), 2.15 (multiplet, 1 proton), 2.18 (quartet, 2 protons), 2.52 (multiplet, 1 proton), 2.65 (multiplet, 1 proton), 2.78 (multiplet, 1 proton), 3.60 (multiplet, 2 protons), 3.85 (multiplet, 2 protons), 4.96 (doublet of doublets, 1 proton), 5.02 (doublet, 1 proton), 5.20 (doublet, 1 proton), 5.61 (doublet of doublets, 1 proton), 5.66 (singlet, 1 proton), 5.69 (doublet of doublets, 1 proton), 5.98 (doublet, 1 proton), 5.99 (doublet, 1 proton), and 6.93 (doublet of doublets, 1 proton) parts per million downfield from tetramethylsilane; and (h) a 90.5 MHz $^{13}$C nuclear magnetic resonance spectrum in deuterochloroform solution showing principal signals at 214.97, 170.60, 164.40, 160.95, 151.97, 139.36, 135.62 134.90, 130.26 138.90, 122.69, 122.08, 120.03, 116.81, 81.55, 73.99, 62.61, 53.84, 47.96, 45.66, 40.82, 33.64, 33.56, 32.22, 26.61, 20.92, 18.67, 13.63, 13.58, 13.33, 12.39, and 12.32 parts per million downfield from tetramethylsilane.

2. A pharmaceutical composition comprising compound CL-1957B as defined by claim 1 in combination with a pharmaceutically acceptable carrier.

* * * * *